United States Patent
Roy et al.

(10) Patent No.: US 9,381,354 B2
(45) Date of Patent: Jul. 5, 2016

(54) VISUAL PROSTHESIS WITH INTEGRATED VISOR AND VIDEO PROCESSING UNIT

(75) Inventors: Arup Roy, Valencia, CA (US); Sanjay Gaikwad, Valencia, CA (US); Kelly H. McClure, Simi Valley, CA (US); Timothy M. Nugent, Santa Monica, CA (US); Robert J. Greenberg, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

(21) Appl. No.: 13/571,244

(22) Filed: Aug. 9, 2012

(65) Prior Publication Data
US 2014/0046400 A1     Feb. 13, 2014

(51) Int. Cl.
*A61N 1/36*     (2006.01)
*A61N 1/05*     (2006.01)

(52) U.S. Cl.
CPC .......... *A61N 1/36046* (2013.01); *A61N 1/0543* (2013.01)

(58) Field of Classification Search
CPC ........... A61N 1/36046; A61N 1/37245; A61N 1/37229; A61N 1/0543; A61N 1/37252; A61N 1/375; A61N 1/37247; G02C 11/06; G02C 11/10; A61F 9/08

USPC ....................................................... 607/53–54
See application file for complete search history.

(56) References Cited

U.S. PATENT DOCUMENTS

| | | | |
|---|---|---|---|
| 3,943,925 A * | 3/1976 | Leight | 128/866 |
| 4,573,481 A | 3/1986 | Bullara | |
| 4,628,933 A | 12/1986 | Michelson | |
| 4,837,049 A | 6/1989 | Byers et al. | |
| 5,109,844 A | 5/1992 | de Juan, Jr. et al. | |
| 5,215,088 A | 6/1993 | Normann et al. | |
| 5,935,155 A | 8/1999 | Humayun et al. | |
| 6,400,989 B1 | 6/2002 | Eckmiller | |
| 6,458,157 B1 | 10/2002 | Suaning | |
| 7,431,450 B2 * | 10/2008 | Huang | 351/103 |
| 2007/0030442 A1 * | 2/2007 | Howell et al. | 351/158 |
| 2008/0144854 A1 * | 6/2008 | Abreu | 381/74 |
| 2008/0154337 A1 * | 6/2008 | McClure et al. | 607/54 |
| 2008/0183244 A1 * | 7/2008 | Greenberg et al. | 607/54 |
| 2010/0045928 A1 * | 2/2010 | Levy | 351/158 |

* cited by examiner

*Primary Examiner* — Catherine Voorhees
(74) *Attorney, Agent, or Firm* — Scott B. Dunbar

(57) ABSTRACT

The present invention is a new configuration for the external portion of a visual prosthesis in the form of a visor or glasses, including a frame supported by a user's nose and ears. The video processing unit is adapted to be connected by temple portions of the visor and rest on the user's upper back behind the user's neck, or behind the user's head. Controls for the video processor are on one or both temple portions of the visor.

9 Claims, 17 Drawing Sheets

VISUAL PROSTHESIS WITH INTEGRATED VISOR AND VIDEO PROCESSING UNIT

CROSS REFERENCE TO RELATED APPLICATIONS

This application is related to U.S. patent application Ser. No. 29/291,134, filed Aug. 15, 2007, for Video Processing Unit for Visual Prosthetic Apparatus; US-2008-0154336-A1, filed Aug. 15, 2007, for Visor for a Visual Prosthesis; and 2009-0118794-A1 filed Nov. 7, 2007 for Video Processing Unit for Visual Prosthetic Apparatus.

FIELD OF THE INVENTION

The present application is related to visual prosthesis, and more particularly to a simpler and more compact external system for a visual prosthesis formed within a single unit worn on the head.

BACKGROUND

In 1755 LeRoy first created a visual perception through electrical stimulation. Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular visual prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretial). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Normann describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal array to the retina. U.S. Pat. No. 5,109,844 to de Juan describes a flat electrode array placed against the retina for visual stimulation. U.S. Pat. No. 5,935,155 to Humayun describes a visual prosthesis for use with the flat retinal array described in de Juan.

SUMMARY

The present invention is a new configuration for the external portion of a visual prosthesis in the form of a visor or glasses, including a frame supported by a user's nose and ears. The video processing unit is adapted to be connected by temple portions of the visor and rest on the user's upper back behind the user's neck, or behind the user's head. Controls for the video processor are on one or both temple portions of the visor.

BRIEF DESCRIPTION OF THE FIGURES

FIGS. 11-1, 11-2, 11-3 and 11-4 show an exemplary embodiment of a video processing unit. FIG. 11-1 should be viewed at the left of FIG. 11-2. FIG. 11-3 should be viewed at the left of FIG. 11-4. FIGS. 11-1 and 11-2 should be viewed on top of FIGS. 11-3 and 14-4.

DETAILED DESCRIPTION

Figure 1:
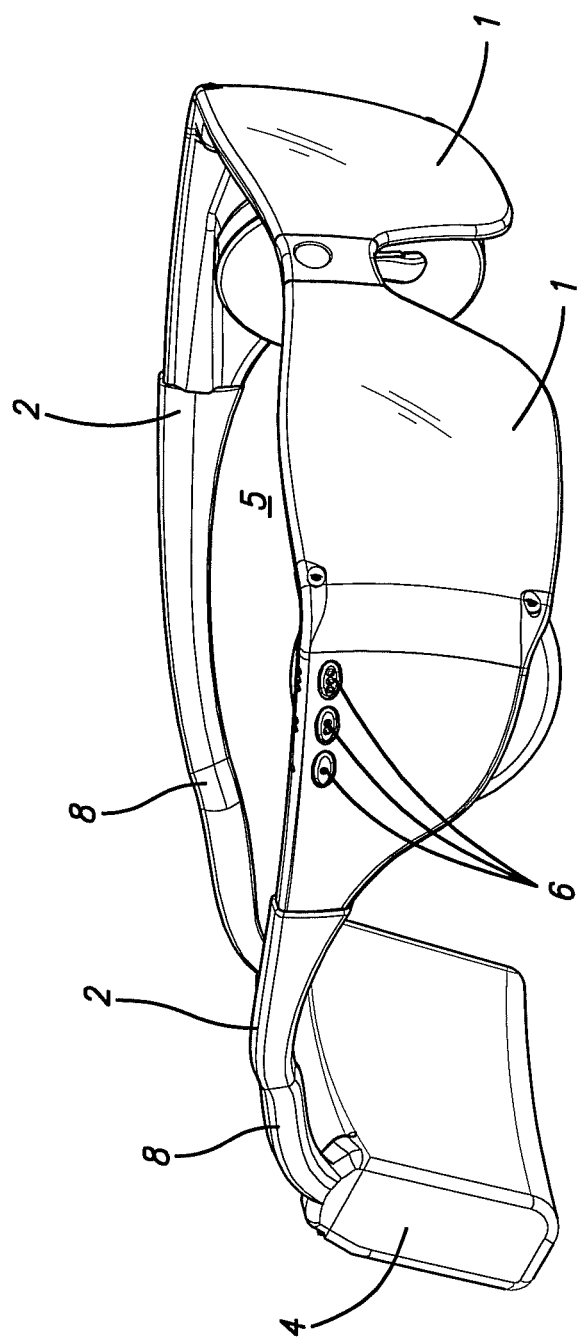
FIG. 1 is a perspective view of the external portion of the preferred visual prosthesis.
Figure 2:
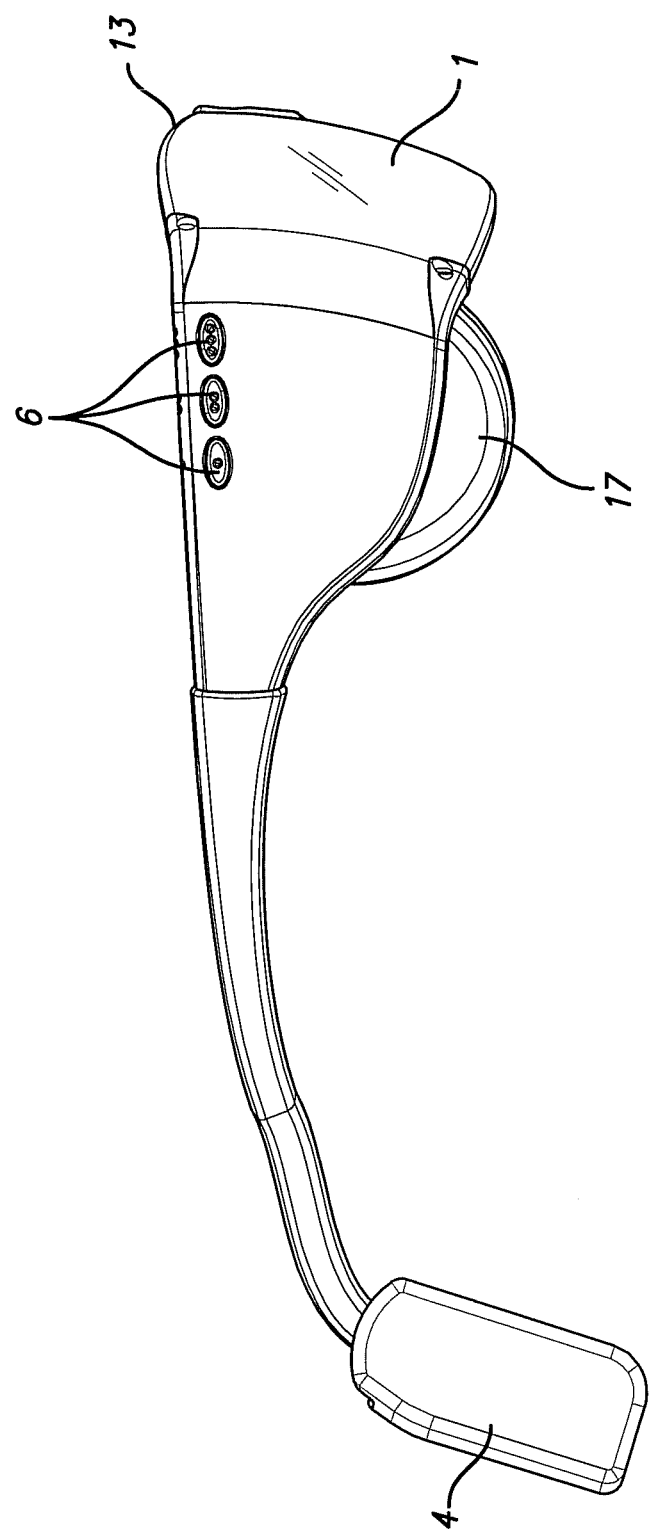
FIG. 2 is a side view of the external portion of the preferred visual prosthesis.
Figure 3:
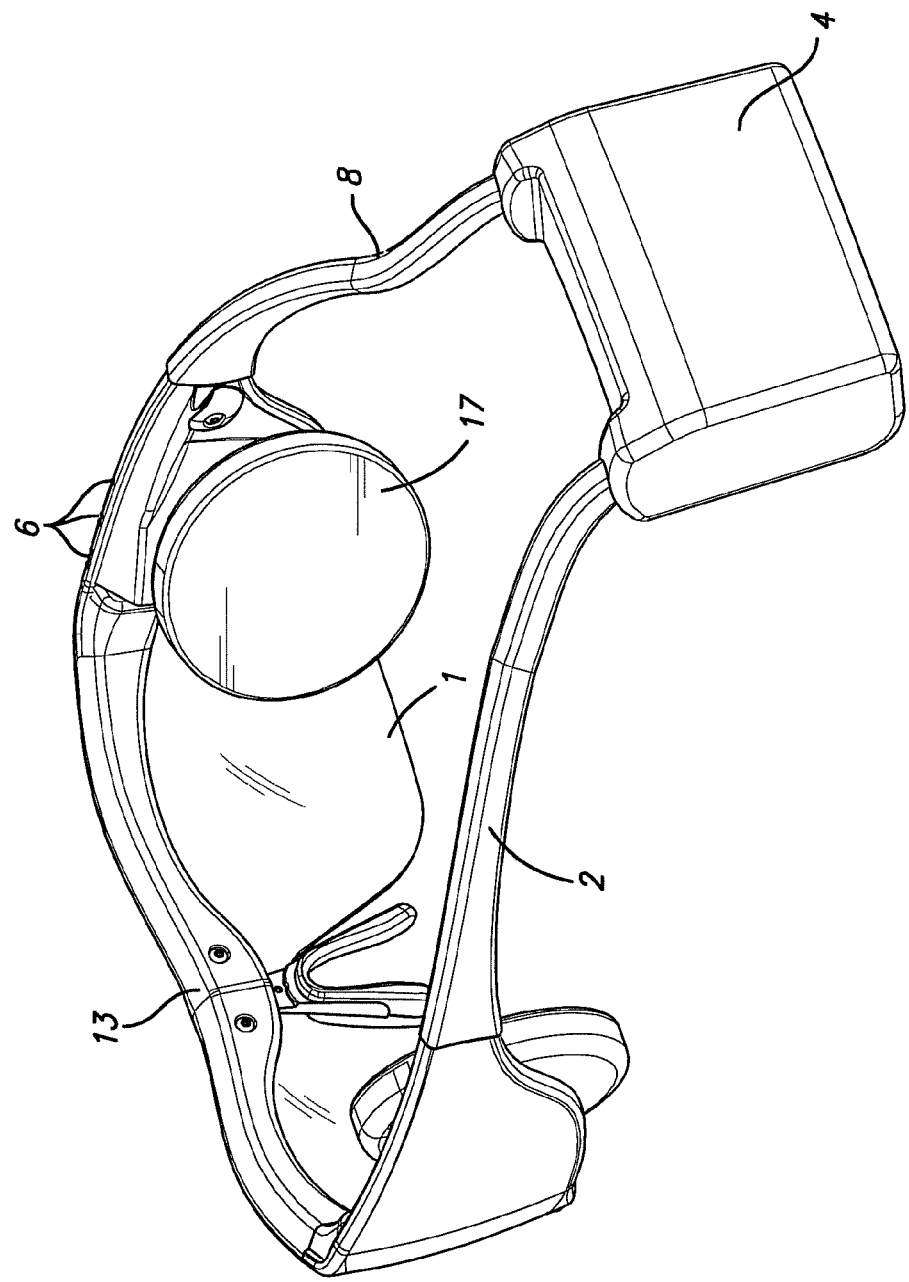
FIG. 3 is a perspective rear view of the external portion of the preferred visual prosthesis.

The present invention is a new configuration for components described in applicant's prior applications: Ser. No. 29/291,134, filed Aug. 15, 2007, for Video Processing Unit for Visual Prosthetic Apparatus; US-2008-0154336-A1, filed Aug. 15, 2007, for Visor for a Visual Prosthesis; and 2009-0118794-A1 filed Nov. 7, 2007 for Video Processing Unit for Visual Prosthetic Apparatus. This present description should be read in light of those prior applications providing details of the components described here in general terms.

FIGS. 1 through 4 provides views of the external portion of a visual prosthesis. The visual prosthesis is in the form of a pair of glasses. The visor has lenses 1, and temples 2. A video processing unit (VPU) 4 is suspended behind the temples such that it will rest, preferably, upon a user's upper back behind their neck. This allows the external portion of the visual prosthesis to be an integrated unit while not supporting the weight of the VPU 4 on the user's ears and nose. Alternatively, the VPU 4 may be worn on the head directly behind the temples. The VPU controls 6 are provided on the temple for easy access. The VPU controls 6 may be on one or both temples. The VPU controls 6 may include common functions such as zoom, brightness, contrast, and saliency functions.

The VPU controls 6 may be programmable according to user preference. The temples 2 have a flexible extension 8 supporting and connecting the VPU 4. This allows the external portion of the visual prosthesis to be slipped over the user's head without the need to disconnect any components of the system. The camera 13 is, preferably, in the bridge of the nose, as in previous versions. The primary coil 17 is mounted to the inside of the temple 2. The primary coil 17 may be on either temple 2 depending in which eye is implanted with the implanted portion of the visual prosthesis.

Figure 5:
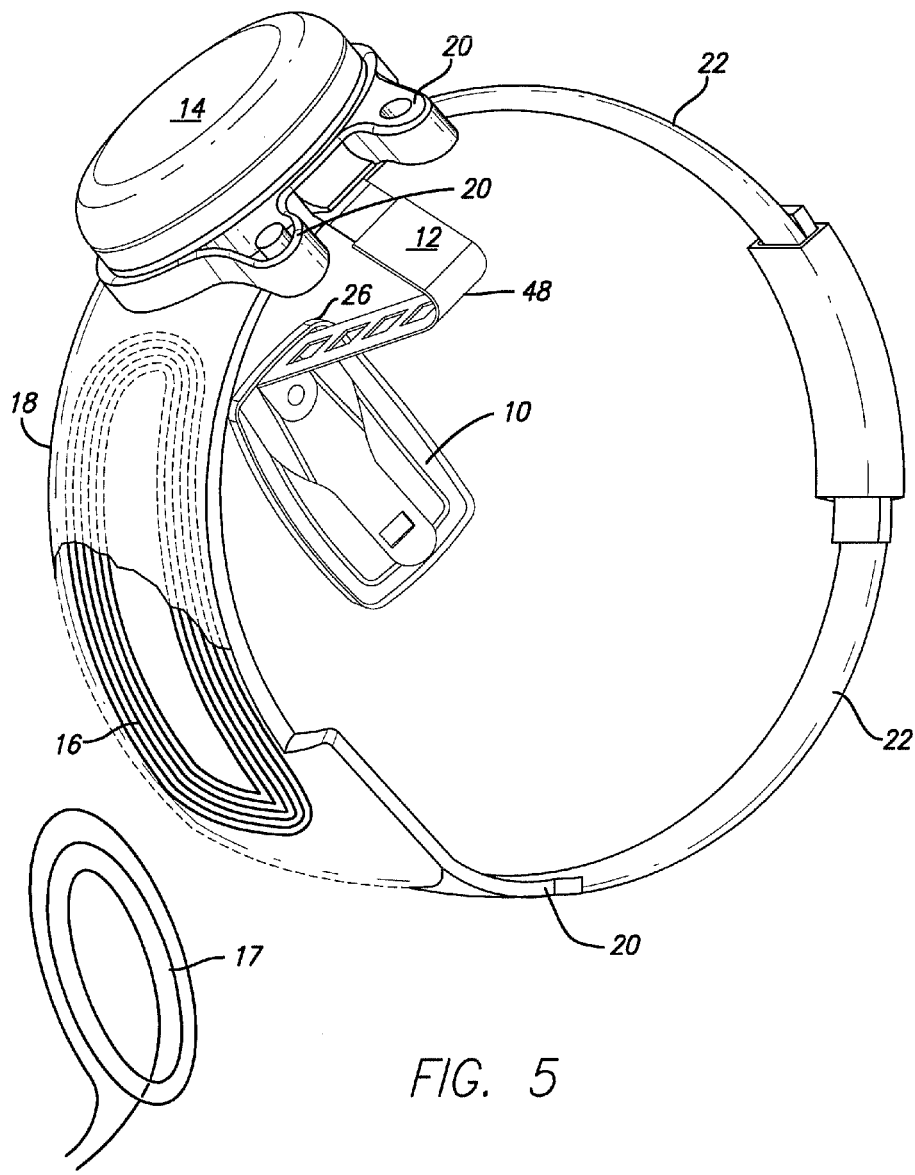
FIGS. 5 and 6 show a retinal stimulation system adapted to be implanted into a subject.
Figure 6:
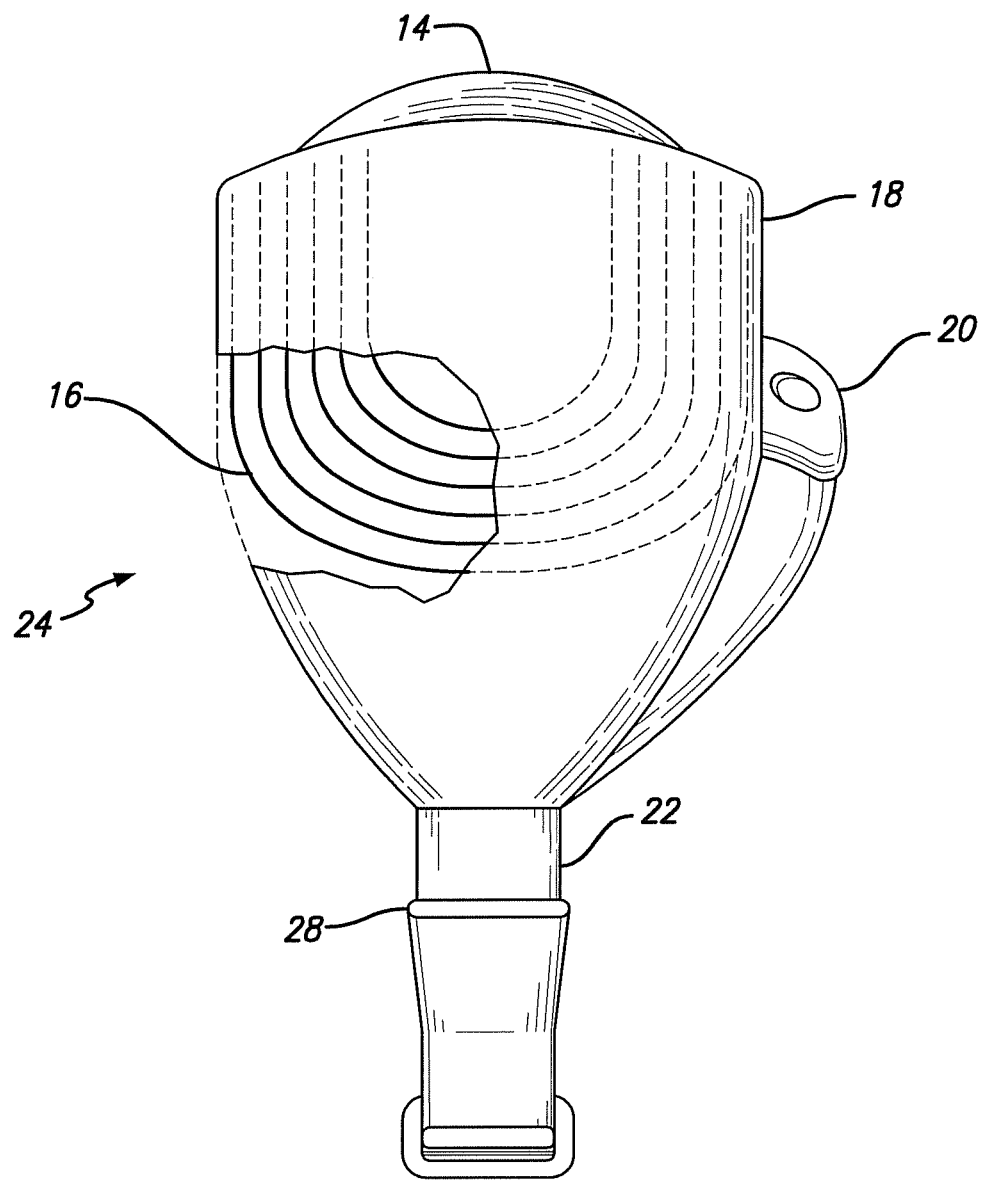

FIGS. 5 and 6 present the general structure of the implant portion of the visual prosthesis used in implementing the invention.

FIG. 5 shows a perspective view of the implanted portion of the preferred visual prosthesis, or retinal stimulation system. A flexible circuit includes a flexible circuit electrode array 10 which is mounted by a retinal tack (not shown) or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The secondary inductive coil receives power and data from a primary inductive coil 17, which is external to the body. The electronics package 14 and secondary inductive coil 16 are held together by the molded body 18. The molded body 18 holds the secondary inductive coil 16 and electronics package 14 in an end to end orientation and minimizes the thickness or height above the sclera of the entire device. The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil. It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

FIG. 6 shows a side view of the implanted portion of the visual prosthesis, in particular, emphasizing the fan tail 24. When implanting the visual prosthesis, it is necessary to pass the strap 22 under the eye muscles to surround the sclera. The secondary inductive coil 16 and molded body 18 must also follow the strap 22 under the lateral rectus muscle on the side of the sclera. The implanted portion of the visual prosthesis is very delicate. It is easy to tear the molded body 18 or break wires in the secondary inductive coil 16. In order to allow the molded body 18 to slide smoothly under the lateral rectus muscle, the molded body 18 is shaped in the form of a fan tail 24 on the end opposite the electronics package 14. The strap 22 further includes a hook 28 the aids the surgeon in passing the strap under the rectus muscles.

Figure 7:
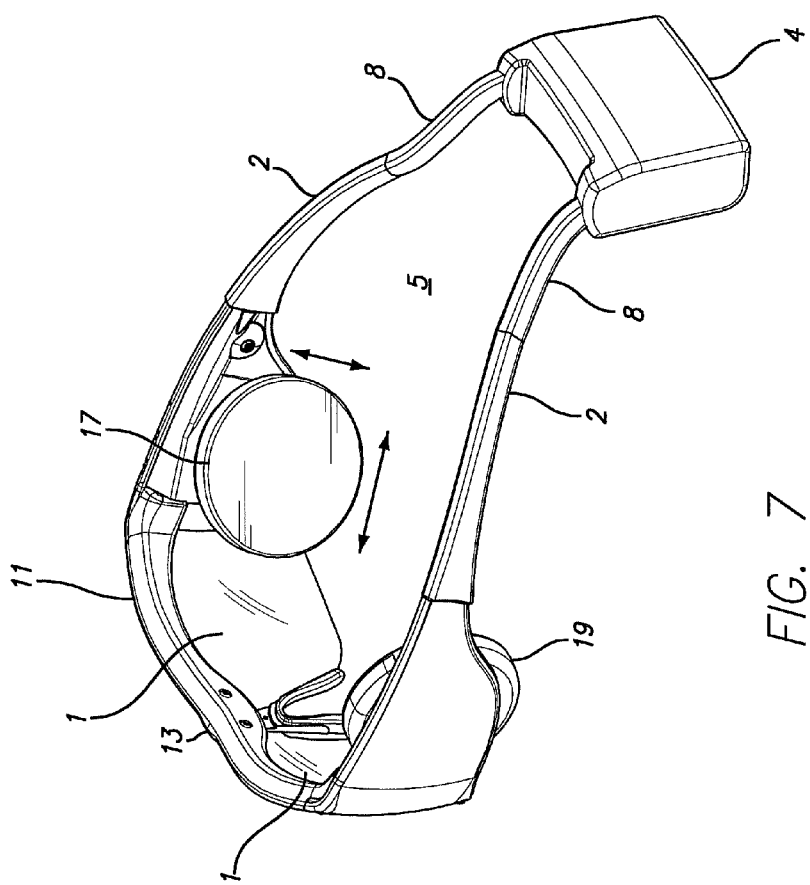
FIGS. 7 and 8 show mechanical portion of the video capture/transmission apparatus or visor shown in FIGS. 1-4 adapted to be used in combination with the retinal stimulation of FIGS. 5 and 6.
Figure 8:
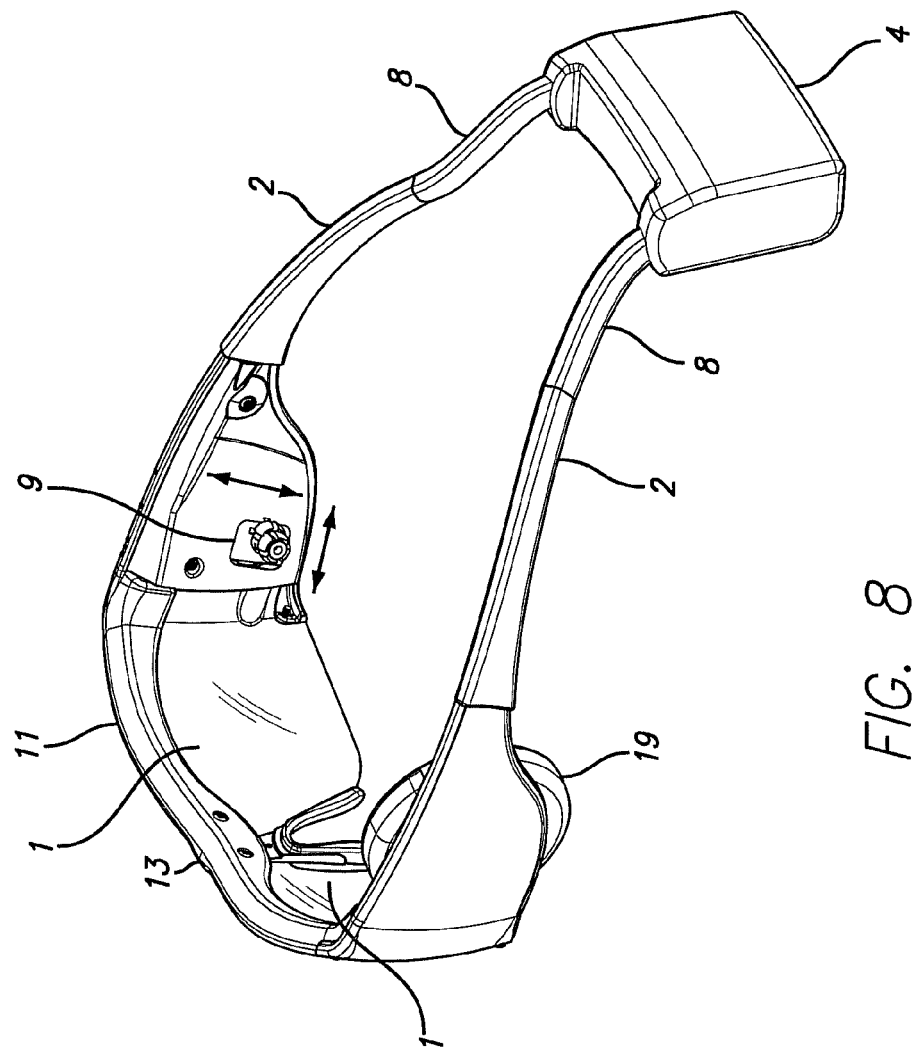

FIGS. 7 and 8 show the mechanical design of the glasses 5 and VPU 4 as shown more generally in FIGS. 1-4 and may comprise, for example, a frame including a lens portion 1 holding a camera 13, a temple portions 2 holding an external coil 17 and a mounting system 9 for the external coil 17, and RF transmitter electronics 19. In this configuration, the video camera 13 captures live video. The video signal is sent to the VPU 4, which processes the video signal and subsequently transforms the processed video signal into electrical stimulation patterns or data. The temple extensions 8, connecting the VPU 4 to the camera 13, transmitter coil 17 and RF electronics 19. The electrical stimulation data are then sent to the external coil 17 that sends both data and power via radio-frequency (RF) telemetry to the coil 16 of the retinal stimulation system, shown in FIGS. 5 and 6. The coil 16 receives the RF commands which control an application specific integrated circuit (ASIC) which in turn delivers stimulation to the retina of the subject via a thin film electrode array (TFEA). In one aspect of an embodiment, light amplitude is recorded by the camera 13. The VPU 4 may use a logarithmic encoding scheme to convert the incoming light amplitudes into the electrical stimulation patterns or data. These electrical stimulation patterns or data may then be passed on to the Retinal Stimulation System, which results in the retinal cells being stimulated via the electrodes in the electrode array 10 (shown in FIGS. 5 and 6). In one exemplary embodiment, the electrical stimulation patterns or data being transmitted by the external coil 17 is binary data. The external coil 17 may contain a receiver and transmitter antennae and a radio-frequency (RF) electronics card for communicating with the internal coil 16. FIG. 8 shows the glasses 5 with the external coil 17 removed to expose the mounting system 9. The external coil, in the preferred embodiment, uses a ball and socket mounting system. A socket on the external coil 17 engages a ball on the temple portion 2. A screw (not shown) through the temple portion 2 expands the ball in the mounting system 9 locking the external coil 17 in place, and locking a sliding plate within the temple portion which adjusts the coil location with respect to the temple portion 2. Hence, the external coil 17 is adjustable within a three dimensional space including angle. This allows the coil to be placed in the optimal relationship to the internal coil 16 for an inductive link.

Figure 9:
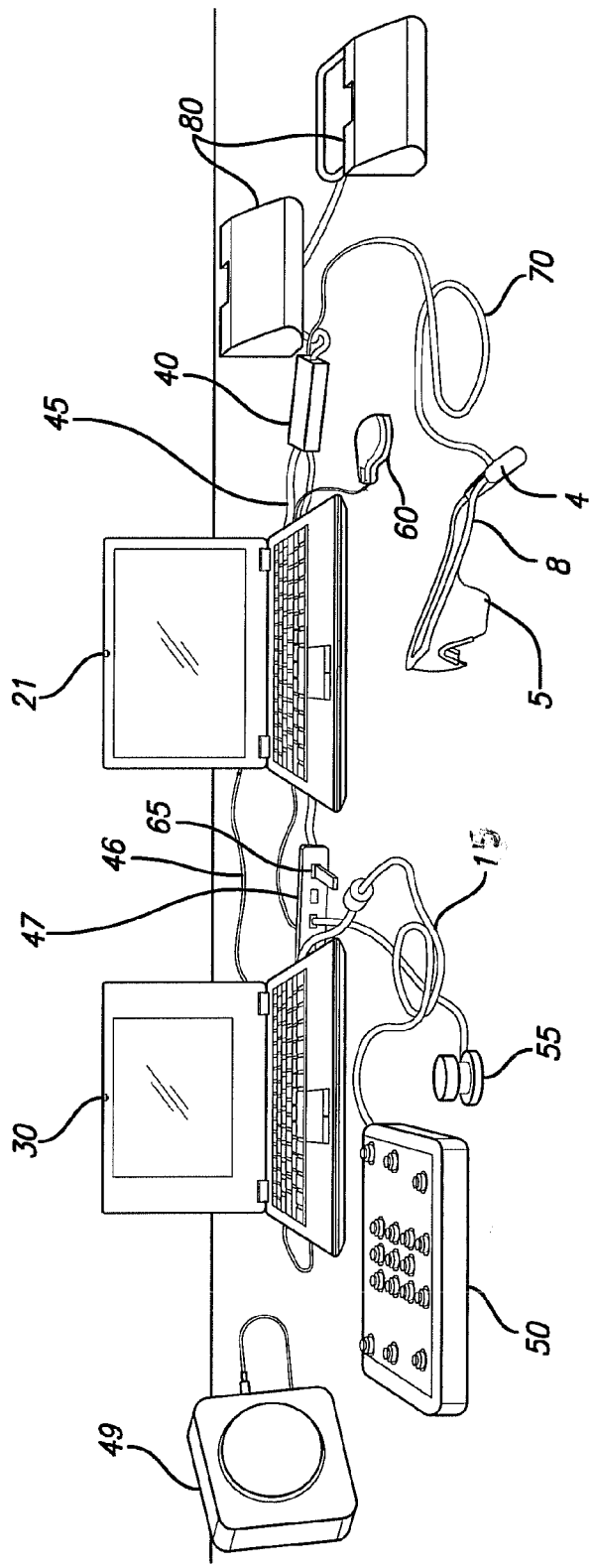
FIG. 9 shows components of a fitting system according to the present disclosure.

Referring to FIG. 9, a Fitting System (FS) may be used to configure and optimize the visual prosthesis apparatus. The Fitting System is fully described in the related application U.S. application Ser. No. 11/796,425, filed on Apr. 27, 2007, which is incorporated herein by reference in its entirety.

The Fitting System may comprise custom software with a graphical user interface running on a dedicated laptop computer 21. Within the Fitting System are modules for performing diagnostic checks of the implant, loading and executing video configuration files, viewing electrode voltage waveforms, and aiding in conducting psychophysical experiments. A video module can be used to download a video configuration file to the VPU (VPU) 4 discussed above and store it in non-volatile memory to control various aspects of video configuration, e.g. the spatial relationship between the video input and the electrodes. The software can also load a previously used video configuration file from the VPU 4 for adjustment.

The Fitting System can be connected to the Psychophysical Test System (PTS), located for example on a dedicated laptop 30, in order to run psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB® (MathWorks®) software and other tools to allow the clinicians to develop customized psychophysics experiment scripts.

Using the psychophysics module, important perceptual parameters such as perceptual threshold, maximum comfort level, and spatial location of percepts may be reliably measured. Based on these perceptual parameters, the fitting software enables custom configuration of the transformation between video image and spatio-temporal electrode stimulation parameters in an effort to optimize the effectiveness of the visual prosthesis for each subject.

The Fitting System laptop 21 of FIG. 9 may be connected to the VPU 4 using an optically isolated serial connection adapter 40. Because it is optically isolated, the serial connection adapter 40 assures that no electric leakage current can flow from the Fitting System laptop 10 in the event of a fault condition.

As shown in FIG. 9, the following components may be used with the Fitting System according to the present disclosure. The Video Processing Unit (VPU) 4 for the subject being tested, the Glasses 5, a Fitting System (FS) Laptop 21, a Psychophysical Test System (PTS) Laptop 30, a PTS CD (not shown), a Communication Adapter (CA) 40, a USB Drive (Security) (not shown), a USB Drive (Transfer) 4-765, a USB Drive (Video Settings) (not shown), a Patient Input Device (RF Tablet) 50, a further Patient Input Device (Jog Dial) 55, RF Tablet Cable 15, CA-VPU Cable 70, FS-CA Cable 45, FS-PTS Cable 46, Four (4) Port USB Hub 47, Mouse 60, Test Array system 80, Archival USB Drive 49, an Isolation Transformer (not shown), adapter cables (not shown), and an External Monitor (not shown).

With continued reference to FIG. 9, the external components of the Fitting System may be configured as follows. The PTS Laptop 30 is connected to FS Laptop 21 using the FS-PTS Cable 46. The PTS Laptop 30 and FS Laptop 21 are plugged into the Isolation Transformer (not shown) using the Adapter Cables (not shown). The Isolation Transformer is plugged into the wall outlet. The four (4) Port USB Hub 47 is connected to the FS laptop 21 at the USB port. The mouse 60 and the two Patient Input Devices 50 and 55 are connected to four (4) Port USB Hubs 47. The FS laptop 21 is connected to the Communication Adapter (CA) 40 using the FS-CA Cable 45. The CA 40 is connected to the VPU 4 using the CA-VPU Cable 70. The Glasses 5 are connected to the VPU 4 using the temple extensions 8.

In one exemplary embodiment, the Fitting System shown in FIG. 9 may be used to configure system stimulation parameters and video processing strategies for each subject outfitted with the visual prosthesis apparatus. The fitting application, operating system, laptops 21 and 30, isolation unit and VPU 4 may be tested and configuration controlled as a system. The software provides modules for electrode control, allowing an interactive construction of test stimuli with control over amplitude, pulse width, and frequency of the stimulation waveform of each electrode in the Retinal stimulation system. These parameters are checked to ensure that maximum charge per phase limits, charge balance, and power limitations are met before the test stimuli are presented to the subject. Additionally, these parameters may be checked a second time by the VPU 4's firmware. The Fitting System shown in FIG. 9 may also provide a psychophysics module for administering a series of previously determined test stimuli to record subject's responses. These responses may be indicated by a keypad 50 and/or verbally. The psychophysics module may also be used to reliably measure perceptual parameters such as perceptual threshold, maximum comfort level, and spatial location of percepts. These perceptual parameters may be used to custom configure the transformation between the video image and spatio-temporal electrode stimulation parameters thereby optimizing the effectiveness of the visual prosthesis for each subject. The Fitting System is fully described in the related application U.S. application Ser. No. 11/796,425, filed on Apr. 27, 2007, which is incorporated herein by reference in its entirety.

The visual prosthesis apparatus may operate in two modes: i) stand-alone mode and ii) communication mode.

Stand-Alone Mode

Figure 10A:
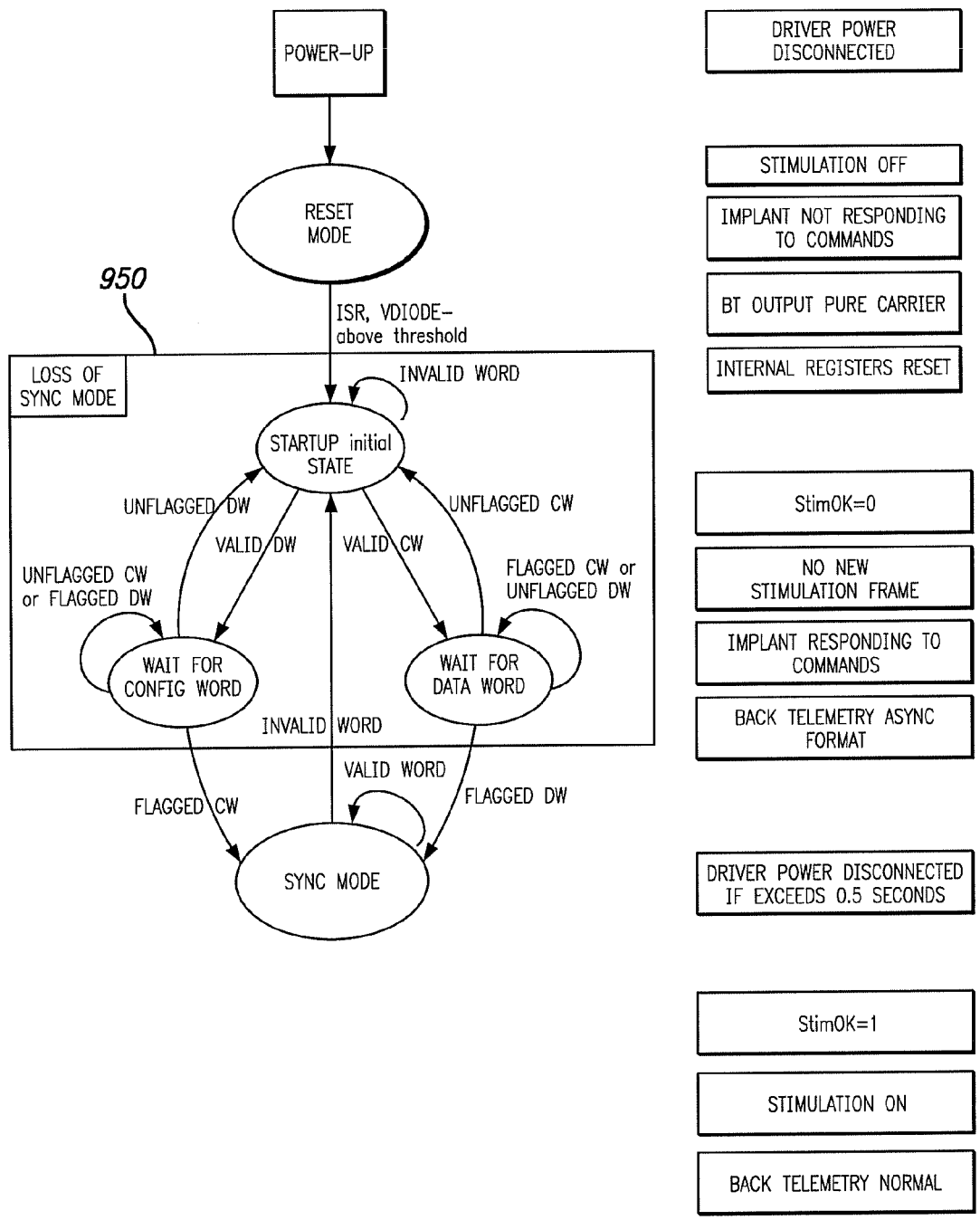
FIG. 10a shows a LOSS OF SYNC mode.
Figure 10B:
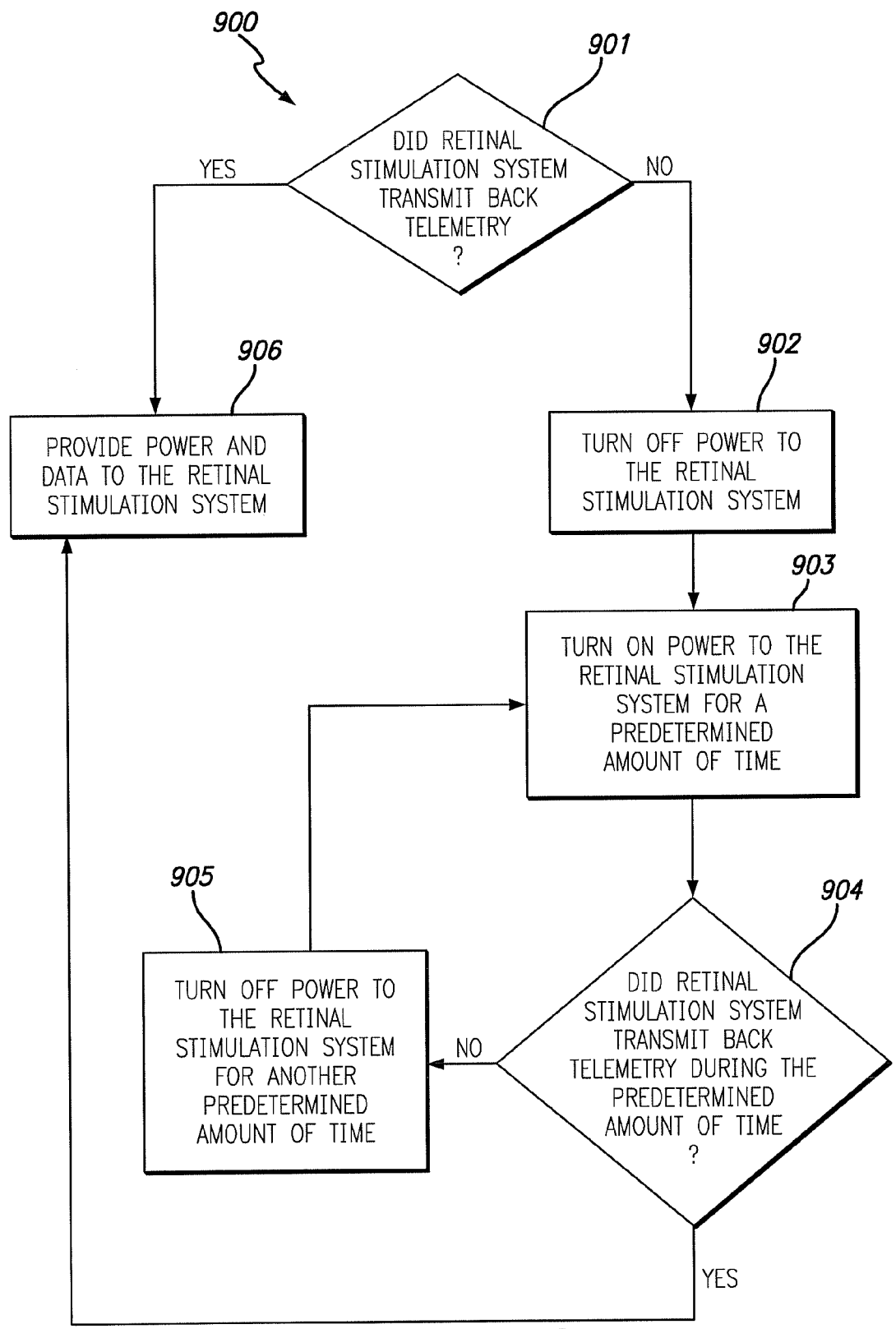
FIG. 10b shows an exemplary block diagram of the steps taken when video processing unit (VPU) does not receive back telemetry from the Retinal stimulation system.
Figure 10C:
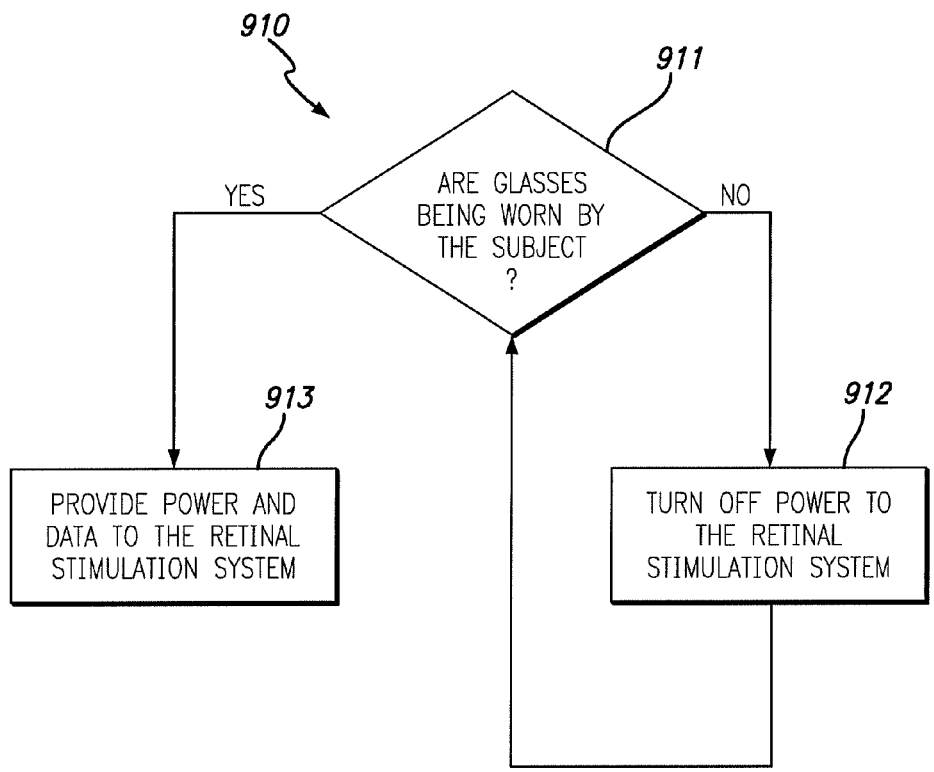
FIG. 10c shows an exemplary block diagram of the steps taken when the subject is not wearing Glasses.

Referring to FIG. 10A through 10C, in the stand-alone mode, the video camera 13, on the glasses 5, captures a video image that is sent to the VPU 4. The VPU 4 processes the image from the camera 13 and transforms it into electrical stimulation patterns that are transmitted to the external coil 17. The external coil 17 sends the electrical stimulation patterns and power via radio-frequency (RF) telemetry to the implanted retinal stimulation system. The internal coil 16 of the retinal stimulation system receives the RF commands from the external coil 17 and transmits them to the electronics package 14 that in turn delivers stimulation to the retina via the electrode array 10. Additionally, the retinal stimulation system may communicate safety and operational status back to the VPU 4 by transmitting RF telemetry from the internal coil 16 to the external coil 17. The visual prosthesis apparatus may be configured to electrically activate the retinal stimulation system only when it is powered by the VPU 4 through the external coil 17. The stand-alone mode may be used for clinical testing and/or at-home use by the subject.

Communication Mode

The communication mode may be used for diagnostic testing, psychophysical testing, patient fitting and downloading of stimulation settings to the VPU 4 before transmitting data from the VPU 4 to the retinal stimulation system as is done for example in the stand-alone mode described above. Referring to FIG. 9, in the communication mode, the VPU 4 is connected to the Fitting System laptop 21 using cables 70, 45 and the optically isolated serial connection adapter 40. In this mode, laptop 21 generated stimuli may be presented to the subject and programming parameters may be adjusted and downloaded to the VPU 4. The Psychophysical Test System (PTS) laptop 30 connected to the Fitting System laptop 21 may also be utilized to perform more sophisticated testing and analysis as fully described in the related application U.S. application Ser. No. 11/796,425, filed on Apr. 27, 2007, which is incorporated herein by reference in its entirety.

In one embodiment, the functionality of the retinal stimulation system can also be tested pre-operatively and intra-operatively (i.e. before operation and during operation) by using an external coil 17, without the glasses 5, placed in close proximity to the retinal stimulation system. The coil 17 may communicate the status of the retinal stimulation system to the VPU 4 that is connected to the Fitting System laptop 21 as shown in FIG. 9.

As discussed above, the VPU 4 processes the image from the camera 13 and transforms the image into electrical stimulation patterns for the retinal stimulation system. Filters such as edge detection filters may be applied to the electrical stimulation patterns for example by the VPU 4 to generate, for example, a stimulation pattern based on filtered video data that the VPU 4 turns into stimulation data for the retinal stimulation system. The images may then be reduced in resolution using a downscaling filter. In one exemplary embodiment, the resolution of the image may be reduced to match the number of electrodes in the electrode array 10 of the retinal stimulation system. That is, if the electrode array has, for example, sixty electrodes, the image may be reduced to a sixty channel resolution. After the reduction in resolution, the image is mapped to stimulation intensity using for example a look-up table that has been derived from testing of individual subjects. Then, the VPU 4 transmits the stimulation parameters via forward telemetry to the retinal stimulation system in frames that may employ a cyclic redundancy check (CRC) error detection scheme.

In one exemplary embodiment, the VPU 4 may be configured to allow the subject/patient i) to turn the visual prosthesis apparatus on and off, ii) to manually adjust settings, and iii) to provide power and data to the retinal stimulation system. Referring again to FIGS. 1 through 4, the VPU 4 may comprise a case, and button 6 including power button for turning the VPU 4 on and off, setting button, zoom buttons for controlling the camera 13, temple extensions 8 for connecting to the Glasses 5, a connector port for connecting to the laptop 21 through the connection adapter 40, indicator lights (not shown) on the VPU 4 or glasses 5 to give visual indication of operating status of the system, the rechargeable battery (not shown) for powering the VPU 4, battery latch (not shown) for locking the battery in the case, digital circuit boards (not shown), and a speaker (not shown) to provide audible alerts to indicate various operational conditions of the system. Because the VPU 4 is used and operated by a person with minimal or no vision, the buttons on the VPU 4 may be differently shaped and/or have special markings to help the user identify the functionality of the button without having to look at it.

In one embodiment, the indicator lights may indicate that the VPU 4 is going through system start-up diagnostic testing when the one or more indicator lights are blinking fast (more then once per second) and are green in color. The indicator lights may indicate that the VPU 4 is operating normally when the one or more indicator lights are blinking once per second and are green in color. The indicator lights may indicate that the retinal stimulation system has a problem that was detected by the VPU 4 at start-up diagnostic when the one or more indicator lights are blinking for example once per five second and are green in color. The indicator lights may indicate that there is a loss of communication between the retinal stimulation system and the external coil 17 due to the movement or removal of Glasses 5 while the system is operational or if the VPU 4 detects a problem with the retinal stimulation system and shuts off power to the retinal stimulation system when the one or more indicator lights are always on and are orange color. One skilled in the art would appreciate that other colors and blinking patterns can be used to give visual indication of operating status of the system without departing from the spirit and scope of the invention.

In one embodiment, a single short beep from the speaker (not shown) may be used to indicate that one of the buttons 6 have been pressed. A single beep followed by two more beeps from the speaker (not shown) may be used to indicate that VPU 4 is turned off. Two beeps from the speaker (not shown) may be used to indicate that VPU 4 is starting up. Three beeps from the speaker (not shown) may be used to indicate that an error has occurred and the VPU 4 is about to shut down automatically. As would be clear to one skilled in the art, different periodic beeping may also be used to indicate a low battery voltage warning, that there is a problem with the video signal, and/or there is a loss of communication between the retinal stimulation system and the external coil 17. One skilled in the art would appreciate that other sounds can be used to give audio indication of operating status of the system without departing from the spirit and scope of the invention. For example, the beeps may be replaced by an actual prerecorded voice indicating operating status of the system.

In one exemplary embodiment, the VPU 4 is in constant communication with the retinal stimulation system through forward and backward telemetry. In this document, the forward telemetry refers to transmission from VPU 4 to the retinal stimulation system and the backward telemetry refers to transmissions from the Retinal stimulation system to the VPU 4. During the initial setup, the VPU 4 may transmit null frames (containing no stimulation information) until the VPU 4 synchronizes with the Retinal stimulation system via the back telemetry. In one embodiment, an audio alarm may be used to indicate whenever the synchronization has been lost.

In order to supply power and data to the Retinal stimulation system, the VPU 4 may drive the external coil 17, for example, with a 3 MHz signal. To protect the subject, the retinal stimulation system may comprise a failure detection circuit to detect direct current leakage and to notify the VPU 4 through back telemetry so that the visual prosthesis apparatus can be shut down.

The forward telemetry data (transmitted for example at 122.76 kHz) may be modulated onto the exemplary 3 MHz carrier using Amplitude Shift Keying (ASK), while the back telemetry data (transmitted for example at 3.8 kHz) may be modulated using Frequency Shift Keying (FSK) with, for example, 442 kHz and 457 kHz. The theoretical bit error rates can be calculated for both the ASK and FSK scheme assuming a ratio of signal to noise (SNR). The system disclosed in the present disclosure can be reasonably expected to see bit error rates of 10-5 on forward telemetry and 10-3 on back telemetry. These errors may be caught more than 99.998% of the time by both an ASIC hardware telemetry error detection algorithm and the VPU 4's firmware. For the forward telemetry, this is due to the fact that a 16-bit cyclic redundancy check (CRC) is calculated for every 1024 bits sent to the ASIC within electronics package 14 of the Retinal Stimulation System. The ASIC of the Retinal Stimulation System verifies this CRC and handles corrupt data by entering a non-stimulating 'safe' state and reporting that a telemetry error was detected to the VPU 4 via back telemetry. During the 'safe' mode, the VPU 4 may attempt to return the implant to an operating state. This recovery may be on the order of milliseconds. The back telemetry words are checked for a 16-bit header and a single parity bit. For further protection against corrupt data being misread, the back telemetry is only checked for header and parity if it is recognized as properly encoded Bi-phase Mark Encoded (BPM) data. If the VPU 4 detects invalid back telemetry data, the VPU 4 immediately changes mode to a 'safe' mode where the Retinal Stimulation System is reset and the VPU 4 only sends non-stimulating data frames. Back telemetry errors cannot cause the VPU 4 to do anything that would be unsafe. The response to errors detected in data transmitted by VPU 4 may begin at the ASIC of the Retinal Stimulation System. The Retinal Stimulation System may be constantly checking the headers and CRCs of incoming data frames. If either the header or CRC check fails, the ASIC of the Retinal Stimulation System may enter a mode called LOSS OF SYNC 950, shown in FIG. 10*a*. In LOSS OF SYNC mode 950, the Retinal Stimulation System will no longer produce a stimulation output, even if commanded to do so by the VPU 4. This cessation of stimulation occurs after the end of the stimulation frame in which the LOSS OF SYNC mode 950 is entered, thus avoiding the possibility of unbalanced pulses not completing stimulation. If the Retinal Stimulation System remains in a LOSS OF SYNC mode 950 for 1 second or more (for example, caused by successive errors in data transmitted by VPU 4), the ASIC of the Retinal Stimulation System disconnects the power lines to the stimulation pulse drivers. This eliminates the possibility of any leakage from the power supply in a prolonged LOSS OF SYNC mode 950. From the LOSS OF SYNC mode 950, the Retinal Stimulation System will not re-enter a stimulating mode until it has been properly initialized with valid data transmitted by the VPU 4.

In addition, the VPU 4 may also take action when notified of the LOSS OF SYNC mode 950. As soon as the Retinal Stimulation System enters the LOSS OF SYNC mode 950, the Retinal Stimulation System reports this fact to the VPU 4 through back telemetry. When the VPU 4 detects that the Retinal Stimulation System is in LOSS OF SYNC mode 950, the VPU 4 may start to send 'safe' data frames to the Retinal Stimulation System. 'Safe' data is data in which no stimulation output is programmed and the power to the stimulation drivers is also programmed to be off. The VPU 4 will not send data frames to the Retinal Stimulation System with stimulation commands until the VPU 4 first receives back telemetry from the Retinal Stimulation System indicating that the Retinal Stimulation System has exited the LOSS OF SYNC mode 950. After several unsuccessful retries by the VPU 4 to take the implant out of LOSS OF SYNC mode 950, the VPU 4 will enter a Low Power Mode (described below) in which the implant is only powered for a very short time. In this time, the VPU 4 checks the status of the implant. If the implant continues to report a LOSS OF SYNC mode 950, the VPU 4 turns power off to the Retinal Stimulation System and tries again later. Since there is no possibility of the implant electronics causing damage when it is not powered, this mode is considered very safe.

Due to an unwanted electromagnetic interference (EMI) or electrostatic discharge (ESD) event the VPU 4 data, specifically the VPU firmware code, in RAM can potentially get corrupted and may cause the VPU 4 firmware to freeze. As a result, the VPU 4 firmware will stop resetting the hardware watchdog circuit, which may cause the system to reset. This will cause the watchdog timer to expire causing a system reset in, for example, less than 2.25 seconds. Upon recovering from the reset, the VPU 4 firmware logs the event and shuts itself down. VPU 4 will not allow system usage after this occurs once. This prevents the VPU 4 code from freezing for extended periods of time and hence reduces the probability of the VPU sending invalid data frames to the implant.

Supplying power to the Retinal stimulation system can be a significant portion of the VPU 4's total power consumption. When the Retinal stimulation system is not within receiving range to receive either power or data from the VPU 4, the power used by the VPU 4 is wasted.

Power delivered to the Retinal stimulation system may be dependent on the orientation of the coils 17 and 16. The power delivered to the Retinal stimulation system may be controlled, for example, via the VPU 4 every 16.6 ms. The Retinal stimulation system may report how much power it receives and the VPU 4 may adjust the power supply voltage of the RE driver to maintain a required power level on the Retinal stimulation system. Two types of power loss may occur: 1) long term (>~1 second) and 2) short term (<~1 second). The long term power loss may be caused, for example, by a subject removing the Glasses 5.

In one exemplary embodiment, the Low Power Mode may be implemented to save power for VPU 4. The Low Power Mode may be entered, for example, anytime the VPU 4 does not receive back telemetry from the Retinal stimulation system. Upon entry to the Low Power Mode, the VPU 4 turns off power to the Retinal stimulation system. After that, and periodically, the VPU 4 turns power back on to the Retinal stimulation system for an amount of time just long enough for the presence of the Retinal stimulation system to be recognized via its back telemetry. If the Retinal stimulation system is not immediately recognized, the controller again shuts off power to the Retinal stimulation system. In this way, the controller 'polls' for the passive Retinal stimulation system and a significant reduction in power used is seen when the Retinal stimulation system is too far away from its controller device. FIG. 10b depicts an exemplary block diagram 900 of the steps taken when the VPU 4 does not receive back telemetry from the Retinal stimulation system. If the VPU 4 receives back telemetry from the Retinal stimulation system (output "YES" of step 901), the Retinal stimulation system may be provided with power and data (step 906). If the VPU 4 does not receive back telemetry from the Retinal stimulation system (output "NO" of step 901), the power to the Retinal stimulation system may be turned off. After some amount of time, power to the Retinal stimulation system may be turned on again for enough time to determine if the Retinal stimulation system is again transmitting back telemetry (step 903). If the Retinal stimulation system is again transmitting back telemetry (step 904), the Retinal stimulation system is provided with power and data (step 906). If the Retinal stimulation system is not transmitting back telemetry (step 904), the power to the Retinal stimulation system may again be turned off for a predetermined amount of time (step 905) and the process may be repeated until the Retinal stimulation system is again transmitting back telemetry.

In another exemplary embodiment, the Low Power Mode may be entered whenever the subject is not wearing the Glasses 5. In one example, the Glasses 5 may contain a capacitive touch sensor (not shown) to provide the VPU 4 digital information regarding whether or not the Glasses 5 are being worn by the subject. In this example, the Low Power Mode may be entered whenever the capacitive touch sensor detects that the subject is not wearing the Glasses 5. That is, if the subject removes the Glasses 5, the VPU 4 will shut off power to the external coil 17. As soon as the Glasses 5 are put back on, the VPU 4 will resume powering the external coil 17. FIG. 10c depicts an exemplary block diagram 910 of the steps taken when the capacitive touch sensor detects that the subject is not wearing the Glasses 5. If the subject is wearing Glasses 5 (step 911), the Retinal stimulation system is provided with power and data (step 913). If the subject is not wearing Glasses 5 (step 911), the power to the Retinal stimulation system is turned off (step 912) and the process is repeated until the subject is wearing Glasses 5.

Figure 4:
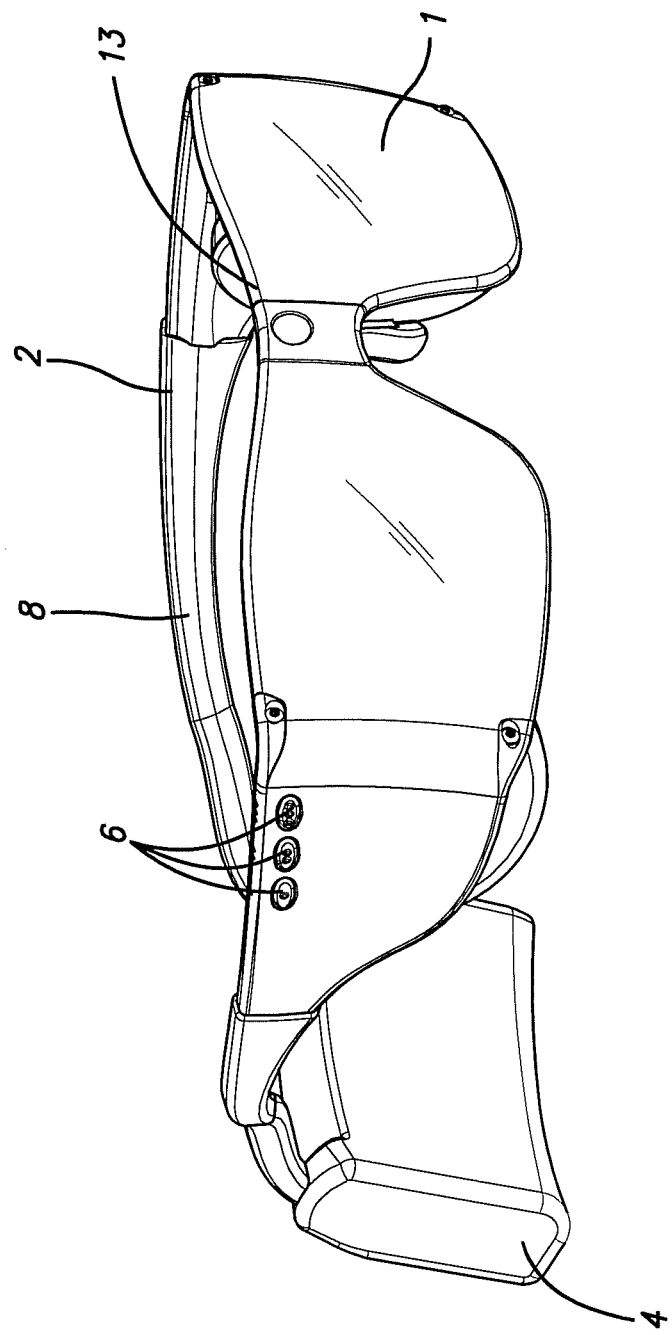
FIG. 4 is a perspective front view of the external portion of the preferred visual prosthesis.
Figures 1, 11:
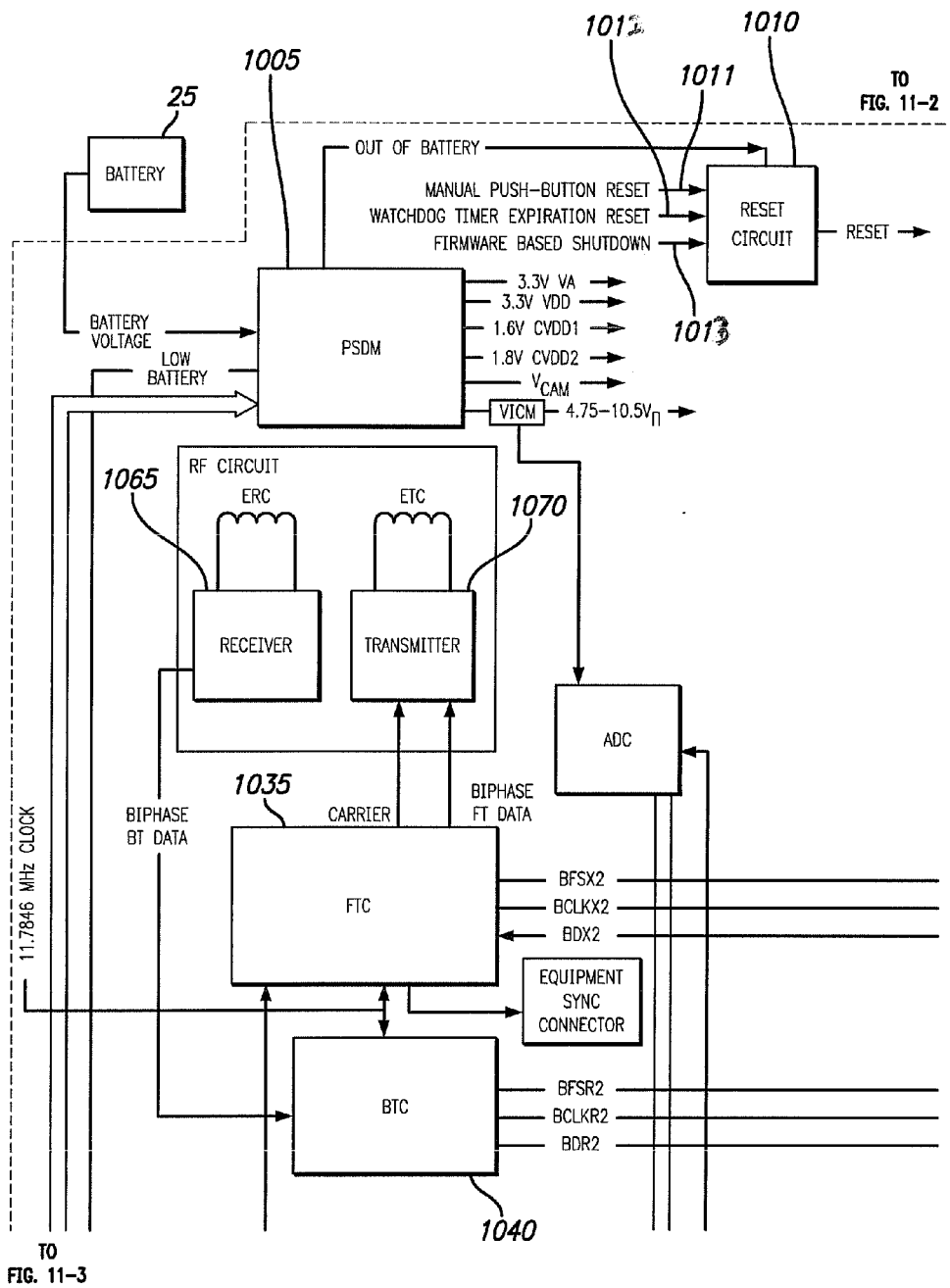
Figures 2, 11:
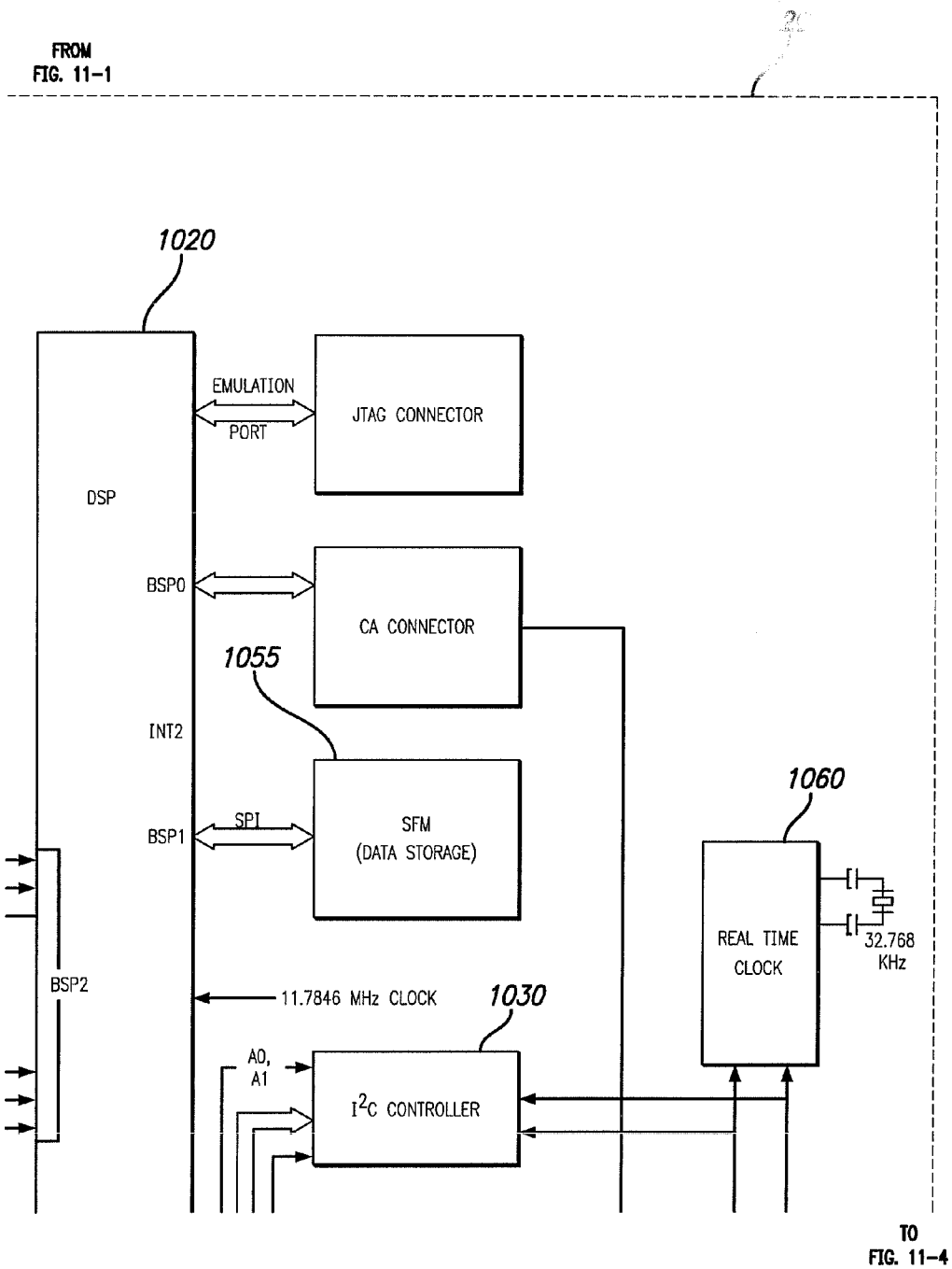
Figures 3, 11:
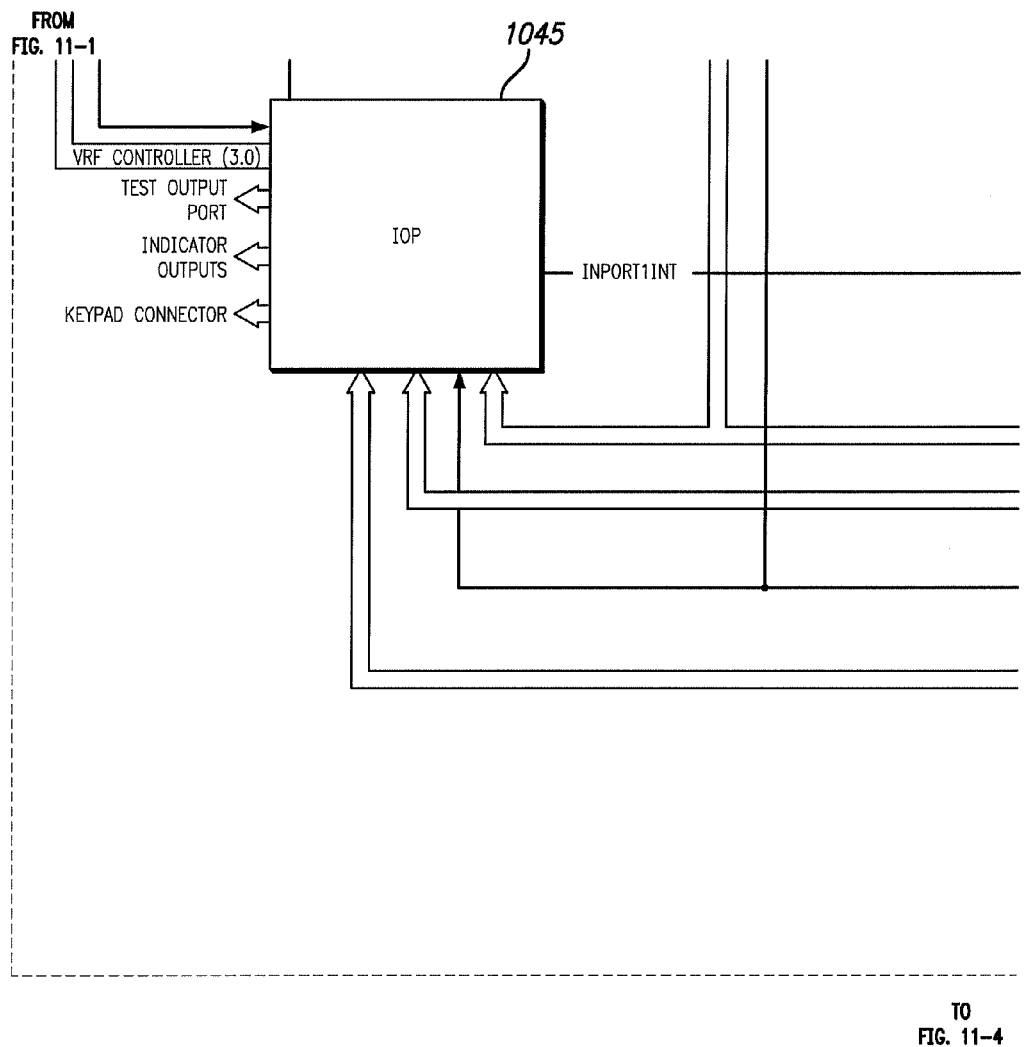
Figures 4, 11:
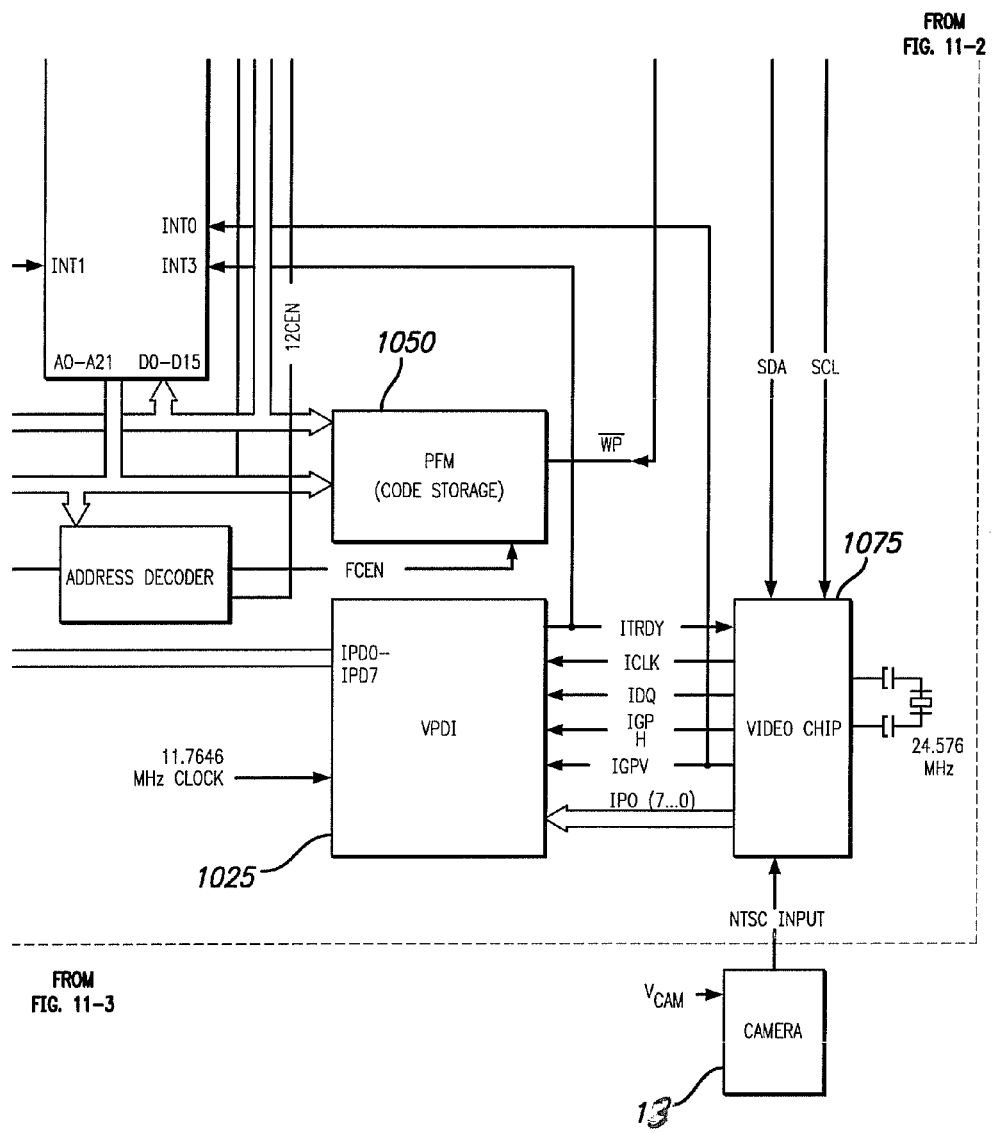

One exemplary embodiment of the VPU 4 is shown in FIG. 11-1 through FIG. 11-4. The VPU 4 may comprise: a Power Supply, a Distribution and Monitoring Circuit (PSDM) 1005, a Reset Circuit 1010, a System Main Clock (SMC) source (not shown), a Video Preprocessor Clock (VPC) source (not shown), a Digital Signal Processor (DSP) 1020, Video Preprocessor Data Interface 1025, a Video Preprocessor 1075, an I²C Protocol Controller 1030, a Complex Programmable Logic device (CPLD) (not shown), a Forward Telemetry Controller (FTC) 1035, a Back Telemetry Controller (BTC) 1040, Input/Output Ports 1045, Memory Devices like a Parallel Flash Memory (PFM) 1050 and a Serial Flash Memory (SFM) 1055, a Real Time Clock 1060, an RF Voltage and Current Monitoring Circuit (VIMC) (not shown), a speaker and/or a buzzer, an RF receiver 1065, and an RF transmitter 1070.

The Power Supply, Distribution and Monitoring Circuit (PSDM) 1005 may regulate a variable battery voltage to several stable voltages that apply to components of the VPU 4. The Power Supply, Distribution and Monitoring Circuit (PSDM) 1005 may also provide low battery monitoring and depleted battery system cutoff. The Reset Circuit 1010 may have reset inputs, a manual push-button reset 1011, a watchdog timer expiration reset 1012, or a firmware based shutdown 1013, that are able to invoke system level rest. For example, the reset inputs 1011 may be from a manual push-button reset, a watchdog timer expiration, and/or firmware based shutdown. The System Main Clock (SMC) source is a clock source for DSP 1020 and CPLD. The Video Preprocessor Clock (VPC) source is a clock source for the Video Processor. The DSP 1020 may act as the central processing unit of the VPU 4. The DSP 1020 may communicate with the rest of the components of the VPU 4 through parallel and serial interfaces. The Video Processor 1075 may convert the NTSC signal from the camera 13 into a down-scaled resolution digital image format. The Video Processor 1075 may comprise a video decoder (not shown) for converting the NTSC signal into high-resolution digitized image and a video scaler (not shown) for scaling down the high-resolution digitized image from the video decoder to an intermediate digitized image resolution. The video decoder may be composed of an Analog Input Processing, Chrominance and Luminance Processing and Brightness Contrast and Saturation (BSC) Control circuits. The video scaler may be composed of Acquisition control, Pre-scaler, BSC-control, Line Buffer and Output Interface. The I²C Protocol Controller 1030 may serve as a link between the DSP 1020 and the I²C bus. The I²C Protocol Controller 1030 may be able to convert the parallel bus interface of the DSP 1020 to the I²C protocol bus or vice versa. The I²C Protocol Controller 1030 may also be connected to the Video Processor 1075 and the Real Time Clock 1060. The VPDI 1025 may contain a tri-state machine to shift video data from Video Preprocessor 1075 to the DSP 1020. The Forward Telemetry Controller (FTC) 1035 packs 1024 bits of forward telemetry data into a forward telemetry frame. The FTC 1035 retrieves the forward telemetry data from the DSP 1020 and converts the data from logic level to biphase marked data. The Back Telemetry Controller (BTC) 1040 retrieves the biphase marked data from the RF receiver 1065, decodes it, and generates the BFSR, BCLKR and BDR for the DSP 1020. The Input/Output Ports 1045 provide expanded IO functions to access the CPLD on-chip and off-chip devices. The Parallel Flash Memory (PFM) 1050 may be used to store executable code and the Serial Flash Memory (SFM) 1055 may provide Serial Port Interface (SPI) for data storage. The VIMC may be used to sample and monitor RF transmitter 1070 current and voltage in order to monitor the integrity status of the retinal stimulation system.

Figure 12:
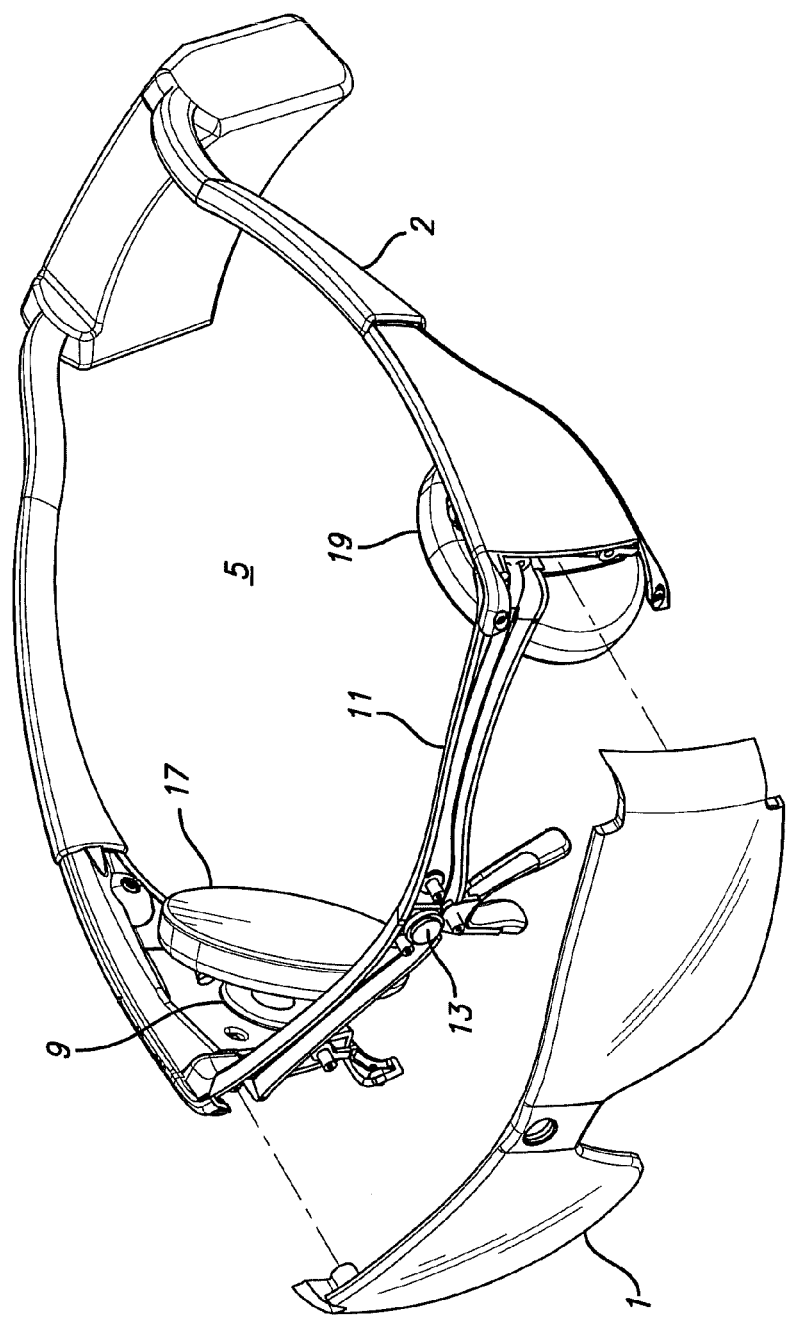
FIG. 12 is a perspective view of the external portion of the preferred visual prosthesis illustrating the removable one piece lens. In the following description, like reference numbers are used to identify like elements. Furthermore, the drawings are intended to illustrate major features of exemplary embodiments in a diagrammatic manner. The drawings are not intended to depict every feature of every implementation nor relative dimensions of the depicted elements, and are not drawn to scale.

FIG. 12 is a perspective view of the external portion of the preferred visual prosthesis illustrating the removable one piece lens. The lens portion of the visor 5 includes a frame 11 holding the camera 13 and a one piece removable lens 1. It is advantageous to provide a removable lens for many reasons. Blind people prefer either clear or dark lenses. Some may prefer clear or dark lenses in different situations. The removable lens also provides for varying tint or color choices. For example, a user may choose a lens to match certain clothing. It would be cost prohibitive to own more than one visor 5. The one piece lens 1 is advantageous over a design with two lenses. The one piece design makes changing lenses easier. Also, the one piece lens 1 makes the whole visor 5 stronger and lighter. The one piece lens 1 reinforces the frame 11 as two separate lenses would not. This allows the visor to be made lighter, and therefore, more comfortable for the user.

Accordingly, what has been shown is an improved visual prosthesis and an improved method for controlling a visual prosthesis. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A visual prosthesis comprising:
a frame suitable to be supported by a user's nose and ears including a lens portion and first and second temple portions;
a camera supported by the frame;
a video processing unit supported by and directly attached to the first and second temple portions receiving data from the camera;
user controls on at least one of the temple portions;
an RF transmitter supported by the frame on a first temple portion receiving data from the video processing unit;
a primary coil supported by the frame on the second temple portion receiving transmission signals from the RF transmitter and suitable to send data to an implantable device.

2. The visual prosthesis according to claim 1, where the video processing unit is suitable to be located behind a user's neck.

3. The visual prosthesis according to claim 1, where the video processing unit is suitable to be located behind a user's head.

4. The visual prosthesis according to claim 2, wherein the camera is supported by the lens portion.

5. The visual prosthesis according to claim 2, further comprising controls for the video processing unit on at least one of the temple portions.

6. The visual prosthesis according to claim 5, wherein the controls include controls selected from the group including zoom, brightness, contrast, and saliency functions including proximity and motion.

7. The visual prosthesis according to claim 2, further comprising flexible extensions of the temple portions connecting the video processing unit to the temple portions.

8. The visual prosthesis according to claim 1, wherein the primary coil is supported by a temple portion.

9. The visual prosthesis according to claim 8, further comprising RF transmitter electronics supported by a temple portion opposite the temple portion supporting the primary coil.

* * * * *